(12) United States Patent
Villamil et al.

(10) Patent No.: US 12,138,466 B2
(45) Date of Patent: Nov. 12, 2024

(54) CABLE-LESS LEAD ADAPTER FOR IMPLANTABLE NEUROSTIMULATOR SYSTEM

(71) Applicant: Greatbatch Ltd., Clarence, NY (US)

(72) Inventors: Luis Daniel Villamil, Montevideo (UY); Mathias de Souza, Montevideo (UY); Ignacio Agustin Armesto, Montevideo (UY)

(73) Assignee: Greatbatch Ltd., Clarence, NY (US)

( * ) Notice: Subject to any disclaimer, the term of this patent is extended or adjusted under 35 U.S.C. 154(b) by 446 days.

(21) Appl. No.: 17/681,891

(22) Filed: Feb. 28, 2022

(65) Prior Publication Data

US 2022/0288400 A1   Sep. 15, 2022

Related U.S. Application Data

(60) Provisional application No. 63/160,050, filed on Mar. 12, 2021.

(51) Int. Cl.
*A61N 1/375* (2006.01)
*H01R 31/06* (2006.01)

(52) U.S. Cl.
CPC ........... *A61N 1/3752* (2013.01); *H01R 31/06* (2013.01); *H01R 2201/12* (2013.01)

(58) Field of Classification Search
CPC ...... A61N 1/3752; A61N 1/754; A61N 1/756; A61N 1/375; A61N 1/3754; A61N 1/3756; H01R 31/06; H01R 2201/12
See application file for complete search history.

(56) References Cited

U.S. PATENT DOCUMENTS

| | | | |
|---|---|---|---|
| 5,199,888 A | 4/1993 | Condra et al. | |
| 6,280,243 B1 | 8/2001 | Liu et al. | |
| 6,466,718 B1 | 10/2002 | Linnell | |
| 6,641,433 B2 | 11/2003 | Devine et al. | |
| 6,719,591 B1 | 4/2004 | Chang | |
| 6,878,013 B1 * | 4/2005 | Behan | H01R 24/58 607/116 |
| 6,923,683 B2 | 8/2005 | Dulai et al. | |
| 6,991,483 B1 | 1/2006 | Milan et al. | |
| 7,083,474 B1 * | 8/2006 | Fleck | H01R 13/5804 439/669 |

(Continued)

*Primary Examiner* — Harshad C Patel
(74) *Attorney, Agent, or Firm* — Michael F. Scalise

(57) ABSTRACT

A lead adapter for a patient treatment system comprises a housing having a plurality of inlets, each inlet being segregated from an immediately adjacent inlet by a housing intermediate wall. A plurality of electrical contact assemblies residing in the housing are electrically connected to a respective one of a plurality of electrical contact posts. Each contact post has an exposed terminal portion residing in one of the plurality of inlets. A header is movably secured to the housing to selectively open and close the housing. With the header in an open position, an implantable lead is movable into a longitudinally extending opening in the header. The header is then manipulatable into a closed position to move an electrical contact of the lead into contact with a respective one of the electrical contact assemblies electrically connected to a respective one of the electrical contact posts. That way, the electrical contacts of the implantable lead are in electrical continuity with an exposed terminal portion of a respective one of the electrical contact posts.

21 Claims, 10 Drawing Sheets

(56) References Cited

U.S. PATENT DOCUMENTS

| | | | |
|---|---|---|---|
| 7,086,898 B2 | 8/2006 | Johnsen et al. | |
| 7,128,614 B1 | 10/2006 | Wu | |
| 7,318,750 B1 | 1/2008 | Chacon et al. | |
| 7,402,076 B1 * | 7/2008 | Lim | H01R 13/5812 |
| | | | 439/462 |
| 7,563,142 B1 * | 7/2009 | Wenger | H01R 13/052 |
| | | | 439/669 |
| 8,133,072 B2 | 3/2012 | Huang et al. | |
| 8,888,500 B2 | 11/2014 | Gao et al. | |
| 8,996,128 B2 * | 3/2015 | Parker | A61N 1/3752 |
| | | | 607/117 |
| 9,088,093 B2 * | 7/2015 | Reisinger | H01R 43/20 |
| 9,089,693 B2 | 7/2015 | Swoyer et al. | |
| 9,226,711 B2 * | 1/2016 | De Jong | A61B 5/0084 |
| 9,687,661 B2 * | 6/2017 | Bortolin | A61N 1/375 |
| 10,653,000 B2 | 5/2020 | Lo et al. | |
| 10,821,290 B2 * | 11/2020 | Villamil | H01R 13/426 |
| 2006/0019542 A1 | 1/2006 | Wu | |
| 2007/0212929 A1 | 9/2007 | Huang et al. | |
| 2009/0099423 A1 | 4/2009 | Al-Ali et al. | |
| 2011/0092081 A1 | 4/2011 | Gao et al. | |
| 2013/0017716 A1 | 1/2013 | Elkhatib et al. | |
| 2013/0115821 A1 | 5/2013 | Golko et al. | |
| 2013/0157500 A1 | 6/2013 | Mattson et al. | |
| 2013/0309901 A1 | 11/2013 | Hilbourne | |
| 2014/0307809 A1 | 10/2014 | Lo | |
| 2016/0118758 A1 | 4/2016 | Cymerman | |
| 2019/0379150 A1 | 12/2019 | Turksu et al. | |
| 2020/0254263 A1 * | 8/2020 | Deininger | A61N 1/375 |
| 2022/0023643 A1 * | 1/2022 | Carter | A61B 18/1485 |

* cited by examiner

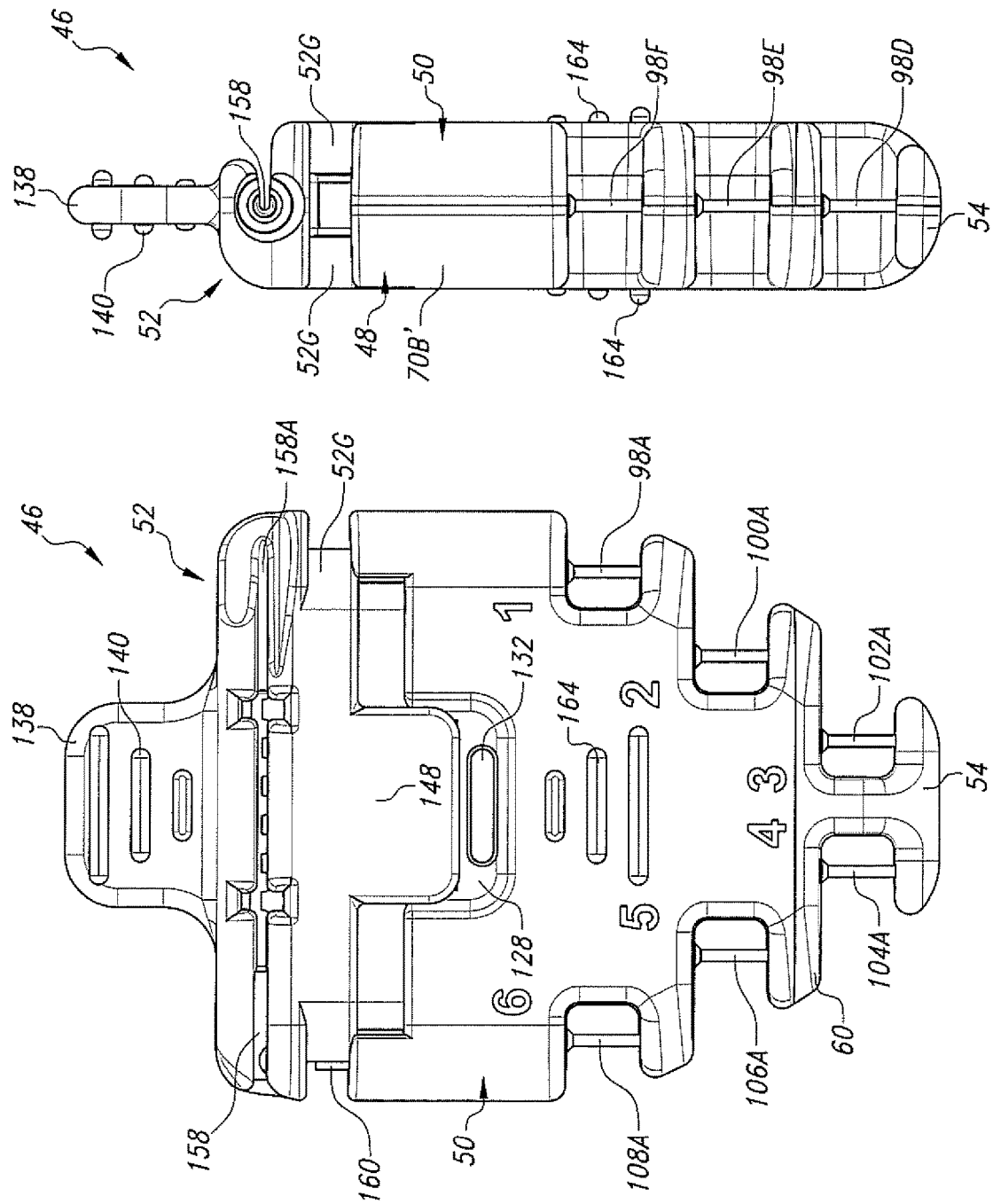

CABLE-LESS LEAD ADAPTER FOR IMPLANTABLE NEUROSTIMULATOR SYSTEM

CROSS-REFERENCE TO RELATED APPLICATION

This application claims the benefit of U.S. provisional patent application Ser. No. 63/160,050, filed on Mar. 12, 2021, the disclosure of which is incorporated herein by reference.

BACKGROUND OF THE INVENTION

Field of the Invention

The present invention relates to implantable medical devices that generate and disperse electrical energy into human or animal body tissues. More particularly, the present invention relates to a lead adaptor for a patient treatment system including an external trial stimulator. The lead adaptor is configured to electrically connect between an implantable lead and an external trial stimulator as a practitioner positions and repositions the lead in a body tissue until the practitioner obtains the desired position for the implantable lead.

Prior Art

The prior art cable assembly for a patient treatment system described in U.S. Pat. No. 10,821,290 to Villamil et al., which is assigned to the assignee of the present invention and incorporated herein by reference, is configured to electrically connect between an implantable lead and an external trial stimulator. The prior art cable assembly has an electrical cable that connects between proximal and distal connectors. The proximal connector has a plurality of electrical contacts that are configured to connect to the external trial stimulator. The distal connector includes a distal housing having an open end. The distal housing houses a manifold that supports a plurality of electrical contact assemblies aligned in two rows, preferably of an equal number of assemblies in each row. The electrical contacts assemblies are spring-loaded assemblies that are electrically connected to a corresponding one of the electrical contacts in the proximal connector via electrical conductors in the cable. The open end of the housing is closed by a header that is movable between a closed position resting or seated on the housing open end and an open position spaced above the housing open end. The header has a pair of side-by-side longitudinally extending openings that are aligned substantially parallel to an imaginary plane in which the distal ends of the plurality of electrical contact assemblies reside.

With the header of the distal connector in the open position, a practitioner (e.g., a physician or a company representative) holds the distal connector in one hand and with the other hand inserts the distal electrical contacts of one or two implantable leads into the longitudinally extending openings of the header. The practitioner then moves the header into the closed position, seated on the open end of the housing of the distal connector. This movement brings the distal electrical contacts of the implantable lead or leads into firm electrical contact with the spring-loaded electrical contact assemblies housed inside the distal connector. The spring-loaded feature for the electrical contact assemblies helps to maintain electrical connections between the electrical contact assemblies of the distal connector and the distal electrical contacts of the one or two implantable leads.

The practitioner then uses the external trial stimulator connected to the proximal connector of the prior art cable assembly to vary the electrical stimulation parameters provided to the leads positioned in a body tissue in real-time. This helps the practitioner select optimal or particularly efficacious parameters including the positions of and the electrical signals provided by the implantable leads. In a typical process, the practitioner uses the prior art cable assembly to temporarily connect the external trial stimulator to the implantable leads to test the efficacy of the leads in an initial position in a body tissue, then disconnects the cable assembly, reposition the leads, and reapplies electrical stimulation. This process is performed iteratively until the practitioner obtains the desired position in the body tissue for the implantable leads.

While the prior art cable assembly described by the '290 patent to Villamil et al. works well for its intended purpose, the proximal connector must be compatible to a particular external trial stimulator. This means that an operating room must keep a number of prior art cable assemblies readily available for connection to any one of a number of external trial stimulators. Having a number of the prior art cable assemblies in stock is a procurement responsibility that can be improved.

SUMMARY OF THE INVENTION

The present invention describes a lead adaptor for a patient treatment system including an external trial stimulator. The lead adaptor, which is configured to electrically connect between an implantable lead and an external trial stimulator, comprises a housing having an open distal end. The housing houses a manifold that supports a plurality of electrical contact assemblies aligned in a row. In a similar manner as with the prior art cable assembly described by the '290 patent to Villamil et al., the electrical contacts assemblies are spring-loaded assemblies that are electrically connected to a corresponding electrical terminal of the lead adapter. The distal open end of the housing is closed by a header that is movable between a closed position resting or seated on the housing open end and an open position spaced above the housing open end. The header has a longitudinally extending opening that is aligned parallel to an imaginary line in which the distal ends of the plurality of electrical contact assemblies reside.

With the header in the open position, a practitioner holds the lead adaptor in one hand and with the other hand inserts the proximal electrical contacts of an implantable lead into the longitudinally extending opening. The practitioner then moves the header into the closed position, seated on the distal open end of the housing. This movement brings the proximal electrical contacts of the implantable lead into firm electrical contact with the spring-loaded electrical contact assemblies housed inside the lead adaptor. The spring-loaded feature for the electrical contact assemblies helps to maintain electrical connections between the electrical contact assemblies of the lead adaptor and the proximal electrical contacts of the implantable lead.

The practitioner then uses the external trial stimulator connected to the proximal housing of the lead adaptor of the present invention to vary the electrical stimulation parameters provided to the implantable lead positioned in a body tissue in real-time. This helps the practitioner select optimal or particularly efficacious parameters including the position of and the electrical signals provided by the implantable lead. In a typical process, the practitioner uses the lead adapter of the present invention to temporarily connect the external trial stimulator to an implantable lead to test the efficacy of the lead in an initial position in a body tissue, then disconnects the lead adapter from the lead, repositions the lead, and reapplies electrical stimulation to the body tissue through the lead. As with the prior art cable assembly of the '290 patent, this process is performed iteratively until the practitioner obtains the desired position for the implantable lead.

However, unlike the prior art cable assembly of the '290 patent, the lead adaptor of the present invention does not have a cable to connect to the external trial stimulator. Instead, the lead adaptor has a number of electrical contact assemblies, each having an exposed terminal that is electrically segregated from an adjacent terminal. That way, a practitioner can electrically connect a lead to an implantable external trial stimulator using an off-the-shelf temporary extension cable, for example, of the type marketed by Oscor Inc., Palm Harbor, Florida, as the ATAR™ D-R D2P connection cable. A suitable temporary extension cable has a proximal end that is configured to connect to any one of a number of different external trial stimulators and a distal alligator clip that is connectable to the exposed terminals of the lead adapter. Immediately adjacent exposed terminals of the lead adapter are segregated from each other by an intermediate wall. The intermediate wall prevents a short-circuit between adjacent alligator clips. In that manner, the lead adapter of the present invention helps to reduce the number of connector-type devices, such as the prior art cable assembly described by the '290 patent to Villamil et al., that must be kept in inventory in a typical operating room.

These and other aspects of the present invention will become increasingly more apparent to those skilled in the art by reference to the following detailed description and to the appended drawings.

BRIEF DESCRIPTION OF THE DRAWINGS

FIG. 13 is a front elevational view of the lead adapter 46 shown in FIG. 3 in an open position.

FIG. 14 is a side elevational view of the open lead adapter 46 shown in FIG. 13.

DETAILED DESCRIPTION OF THE PREFERRED EMBODIMENTS

The description that follows highlights spinal cord stimulation (SCS) systems, the treatment of pelvic floor disorders, and peripheral nerve field stimulation (PNFS). However, it is to be understood that the present invention relates to any type of implantable therapy delivery system with one or more therapy delivery devices, for example, an implantable lead, comprising one or more electrodes or sensors. For example, the present invention may be used as part of a pacemaker, a defibrillator, a cochlear stimulator, a retinal stimulator, a stimulator configured to produce coordinated limb movement, a cortical stimulator, a deep brain stimulator, microstimulator, and in any other neural stimulator configured to treat sleep apnea, shoulder subluxation, headache, and the like.

In another embodiment, one or more of the therapy delivery devices, for example, a catheter, may have a fluid or drug delivery conduit including an inner lumen that is implanted to deliver a fluid, such as pharmaceutical agents, insulin, pain relieving agents, gene therapy agents, and the like, from a fluid delivery system (e.g., a fluid reservoir and/or pump) to a respective target tissue site in a patient.

In yet another embodiment, one or more of the therapy delivery devices may be a medical electrical lead including one or more sensing electrodes to sense physiological parameters (e.g., blood pressure, temperature, cardiac activity, etc.) at a target tissue site within a patient.

In the various embodiments contemplated by the present invention, therapy may include electrical stimulation therapy, sensing or monitoring of one or more physiological parameters, fluid delivery, and the like. The term "implantable lead" includes implantable pacing or defibrillation leads, stimulation leads, sensing leads, fluid delivery catheters, and any combination thereof. The term "target tissue site" refers generally to the target site for implantation of an implantable lead, regardless of the type of therapy.

Figure 1:
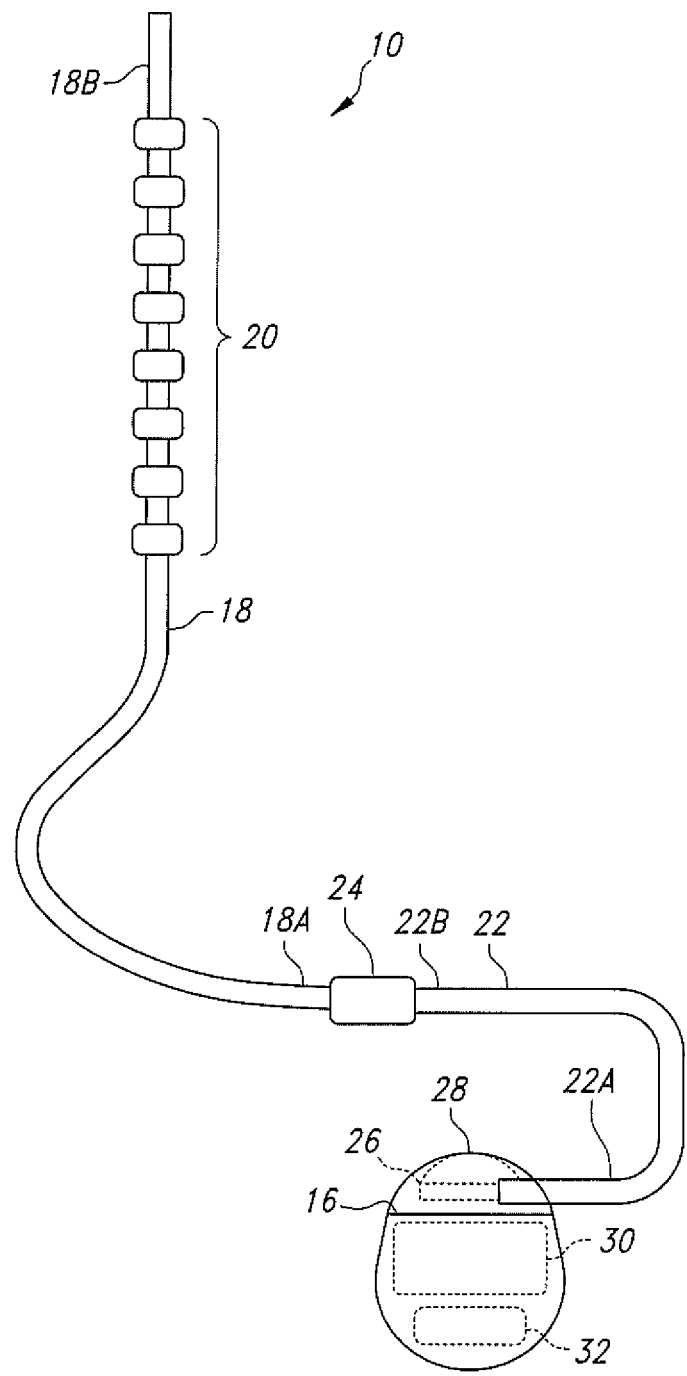
FIG. 1 is a schematic illustration of a therapy delivery system.
Figure 2:
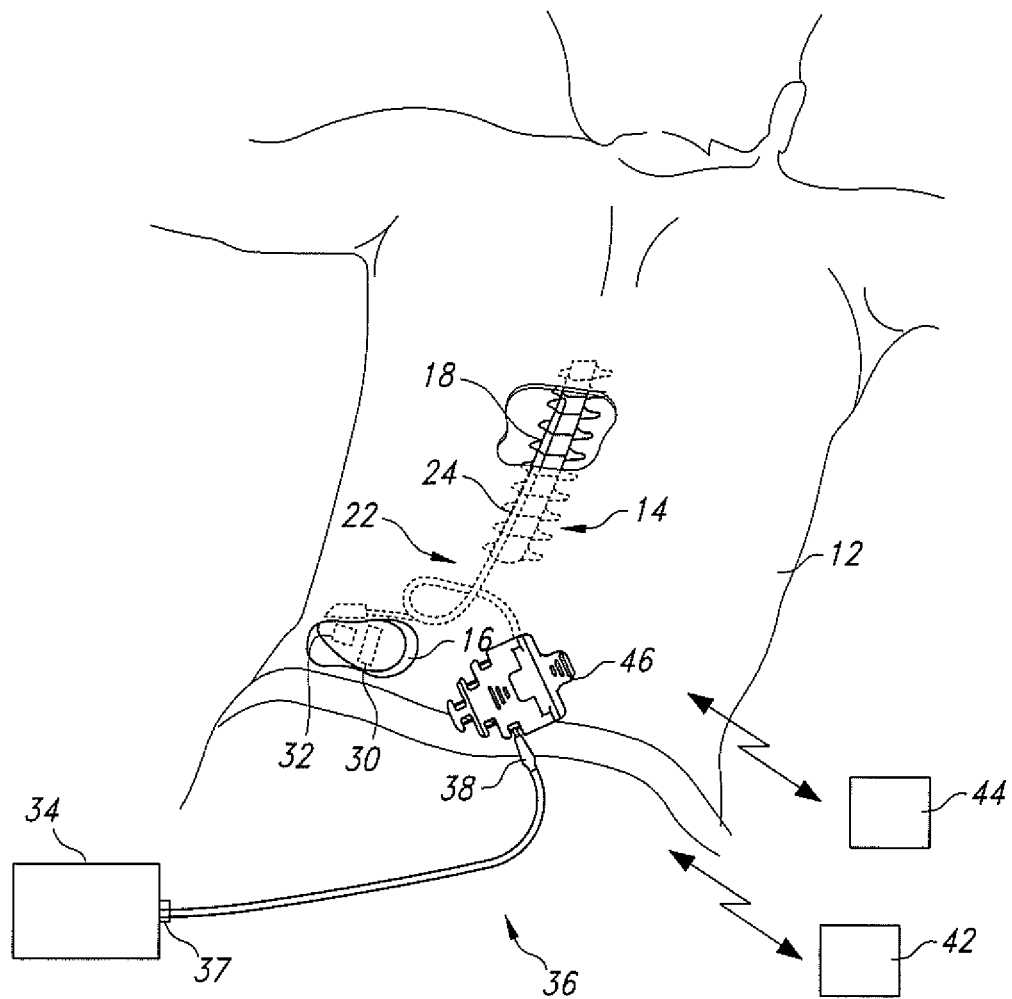
FIG. 2 is a partially schematic illustration of an implantable spinal cord stimulation system positioned at the spine to deliver a therapeutic signal in accordance with an embodiment of the present invention.

Turning now to the drawings, FIGS. 1 and 2 illustrate a generalized therapy delivery system 10 that may be used in electrical stimulation applications, for example for electrical stimulation of a patient's 12 spinal cord 14 representing a target tissue site. The therapy delivery system 10 generally includes an implantable pulse generator 16 ("IPG"), an implantable lead 18, which carries an array of electrodes 20 (shown exaggerated for purposes of illustration), and an optional implantable extension lead 22. The electrodes 20 are typically rings or hollow cylinders that extend around a portion of the circumference of the lead 18. Although only one implantable lead 18 is shown, typically two or more leads are used with the therapy delivery system 10.

The implantable lead 18 representing an exemplary therapy delivery device has a proximal end 18A and a distal end 18B. The implantable lead 18 typically has a diameter ranging from about 0.03 inches to about 0.07 inches and a length ranging from about 30 cm to about 90 cm for spinal cord stimulation applications. The implantable lead 18 may include a suitable electrically insulative coating, such as, a polymeric material (e.g., polyurethane or silicone).

In the illustrated embodiment, the proximal end 18A of the implantable lead 18 is electrically connected to the distal end 22B of the extension lead 22 via a connector 24. The proximal end 22A of the extension lead 22 is in turn electrically connected to the implantable pulse generator 16 via a header connector 26 associated with housing 28. Alternatively, the proximal end 18A of the implantable lead 18 is electrically connected directly to the header connector 26.

In the illustrated embodiment, the implantable pulse generator 16 includes an electronic subassembly 30 (shown schematically), which includes control and pulse generation circuitry (not shown) for delivering electrical stimulation energy to the electrodes 20 of the implantable lead 18 in a controlled manner, and a power supply, such as a battery 32.

The implantable pulse generator 16 provides a programmable stimulation signal (e.g., in the form of an electrical pulse or substantially continuous-time signal) that is delivered to a target stimulation site or sites by the electrodes 20. In applications with more than one implantable lead 18, the implantable pulse generator 16 may provide the same or a different signal to the electrodes 20 of each implantable lead.

The housing 28 is composed of a biocompatible material, for example titanium, and forms a hermetically sealed compartment containing the electronic subassembly 30 and the battery 32 protected from the body tissue and fluids by the compartment. The connector 26 is disposed in a header portion of the housing 28 that is, at least initially, not sealed. The header connector 26 carries a plurality of contacts that electrically connect with respective terminals at the proximal end of the implantable lead 18 or the extension lead 22. Electrical conductors extend from the header connector 26 and connect to the electronic subassembly 30.

Alternatively, the implantable pulse generator 16 can take the form of an implantable receiver-stimulator in which the power source for powering the implanted receiver, as well as control circuitry to command the receiver-stimulator, are contained in an external controller (not shown) inductively coupled to the receiver-stimulator via an electromagnetic link.

As shown in FIG. 2, the implantable pulse generator 16 can take the form of an external trial stimulator (ETS) 34, which has similar pulse generation circuitry as an IPG 16 but differs in that it is a non-implantable device that is used on a trial basis after the lead 18 has been implanted but prior to implantation of the IPG 16. The purpose of the ETS 34 is to test the responsiveness of electrical stimulation that is to be provided by the implantable lead 18.

For example, a practitioner (e.g., a physician or a company representative) can use the external trial stimulator 34 to vary the electrical stimulation parameters provided to the implantable lead 18 in real-time and select optimal or particularly efficacious parameters. These parameters can include the position of the implantable lead 18 with respect to the target tissue site as well as the characteristics of the electrical signals provided to the lead.

In a typical process according to the present invention, the practitioner uses an off-the-shelf temporary extension cable 36 with a proximal male shrouded pin 37 connected to the external trial stimulator 34 and a distal alligator-type clip 38 connected to a lead adapter 46 according to the present invention, which will be described in greater detail hereinafter, to temporarily connect the external trial stimulator to the implantable lead 18. The practitioner can test the efficacy of the lead in an initial position in a body tissue, then disconnect the lead adapter 46, reposition the lead 18, and reapply electrical stimulation. This process is performed iteratively until the practitioner obtains the desired position for the implantable lead 18 in the body tissue. Optionally, the practitioner may move the partially implanted lead 18 without disconnecting the lead adapter 46. In either embodiment, the practitioner will connect and disconnect the lead adapter 46 at least once during the process.

After the position of the implantable lead 18 at the target tissue site and appropriate signal delivery parameters are established using the external trial stimulator 34, the patient 12 receives therapy via electrical signals generated by the external trial stimulator 34, generally for a limited period. In a representative protocol, the patient 12 receives therapy for a one-week trial period. During this time, the patient wears the lead adapter 46 connected to the external trial stimulator 34 by the temporary extension cable 36 outside the body. Assuming the trial therapy is effective or shows the promise of being effective, the practitioner then replaces the external trial stimulator 34 and the connected lead adapter 46 with the implantable pulse generator 16 connected to the implantable lead 18 or connected to the lead extension 22 in turn connected to the lead, and programs the pulse generator 16 with parameters selected based on the experience gained during the trial period. Optionally, the practitioner can also replace the implantable lead 18.

Once the implantable pulse generator 16 is positioned within the patient 12, the signal delivery parameters provided by the implantable pulse generator 16 can still be updated remotely via a physician's wireless programmer 42 (e.g., a physician's remote) or a wireless patient programmer 44 (e.g., a patient remote). Generally, the patient 12 has control over fewer parameters than does the practitioner. For example, the capability of the patient programmer 44 may be limited to starting or stopping the pulse generator 16 or adjusting stimulation amplitude.

FIGS. 3 and 10 to 15 illustrate an assembled lead adapter 46 according to the present invention for use in the generalized therapy delivery system 10 illustrated in FIGS. 1 and 2. The lead adapter 46 comprises an open-ended housing formed from a base plate assembly 48 connected to a cover plate 50. The open-ended housing is closed with a header 52.

Figure 5:
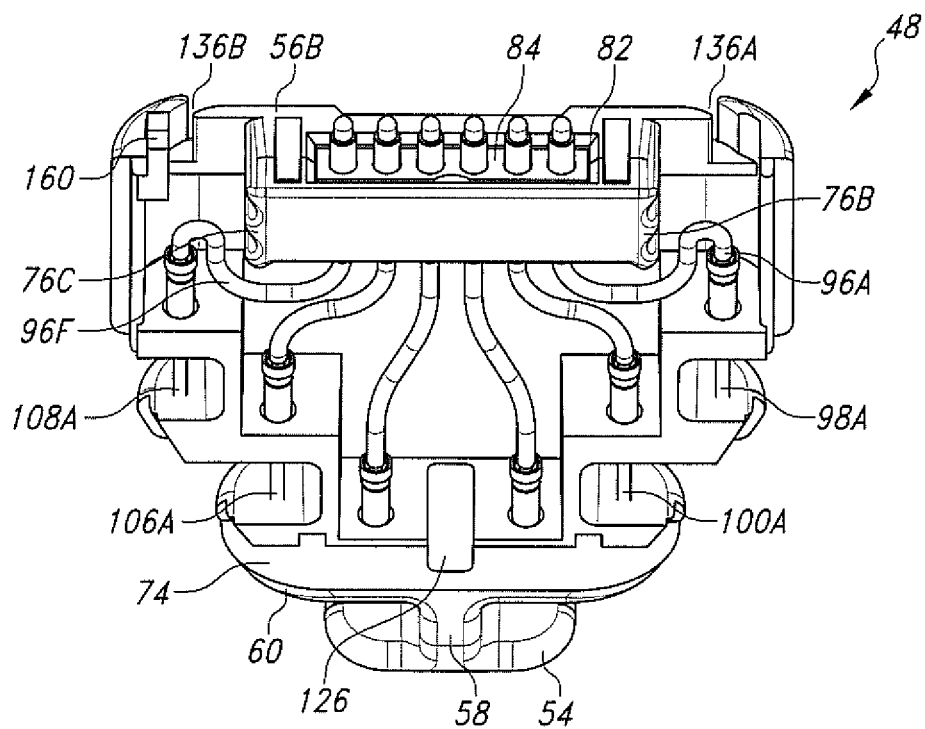
FIG. 5 is a perspective view of the base plate assembly 48 shown in FIG. 3.
Figure 6:
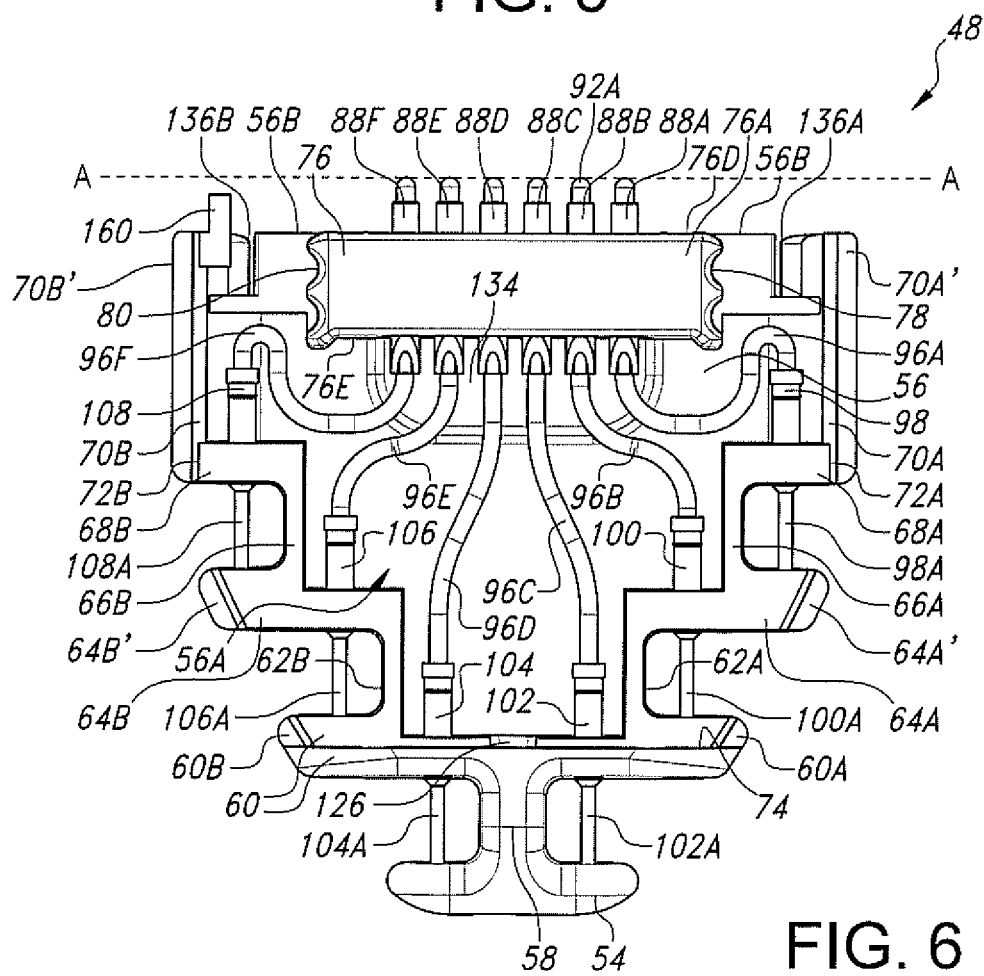
FIG. 6 is a front elevational view of the base plate assembly 48 shown in FIG. 5.

As particularly shown in FIGS. 5 and 6, the base plate assembly 48 has a horizontal base plate foot 54 that is connected to a base plate 56 by a first vertical base extension 58. The base plate 56 has a peripheral edge. A proximal first horizontal base plate wall 60 extends upwardly (out of the plane of the paper on which the drawing is rendered) from the peripheral edge of the base plate 56. The first horizontal base plate wall 60 has opposed steps 60A and 60B.

A first pair of opposed vertical base plate webs 62A and 62B extending upwardly from the peripheral edge of the base plate 56 connect from the proximal first horizontal base plate wall 60 to a second pair of opposed horizontal base plate walls 64A and 64B, which also extend upwardly from the peripheral edge of the base plate 56. The second base plate walls 64A, 64B are provided with respective steps 64A' and 64B'. The opposed second horizontal base plate walls 64A and 64B in turn, connect to a second pair of opposed vertical base plate webs 66A and 66B, which also extend upwardly from the peripheral edge of the base plate 56. The second pair of vertical base plate webs 66A, 66B connect to a third pair of opposed horizontal base plate walls 68A and 68B which, in turn, connect to a third pair of opposed vertical base plate webs 70A and 70B. The third vertical base plate webs 70A, 7B also extend upwardly from the peripheral edge of the base plate 56 and terminate at a distal end of the base plate assembly 48. The third vertical base plate webs 70A and 70B are provided with respective steps 70A' and 70B'.

As shown in FIGS. 5 and 6, the upper edges of the first pair of vertical base plate webs 62A, 62B, the upper edges of the second horizontal base plate walls 64A, 64B, the upper edges of the second pair of vertical base plate webs 66A, 66B, and the upper edges of the third pair of horizontal base plate walls 68A, 68B spaced upwardly (out of the plane of the paper on which the drawing is rendered) from the base plate 56 reside along a first imaginary plane. The first imaginary plane is parallel to the plane of the paper on which the drawing of FIG. 6 is rendered. However, the upper edges of the third pair of vertical base plate webs 70A, 70B spaced from the base plate 56 reside along a second imaginary plane which is recessed toward the inner surface 56A of the base plate 56 with respect to the first imaginary plane by respective steps 72A and 72B.

Further, the upper edges of the proximal first horizontal base plate wall 60, the first vertical base plate extension 58 and the horizontal foot 56 extend upwardly beyond the first imaginary plane. The portion of the proximal first horizontal base plate wall 60 that extends upwardly beyond the first imaginary plane forms a landing area 74 of the first horizontal base plate wall 60 which, as will be described in detail hereinafter, helps support the cover plate 50.

As further shown in FIGS. 5 and 6, a manifold housing 76 is supported by the base plate 56, centered between the third pair of vertical base plate webs 70A, 70B. The manifold housing 76 has a planar front wall 76A spaced from the inner surface 56A of the base plate 56. The manifold housing 76 does not extend the entire width of the base plate 56, instead ending at opposed contoured end walls 76B and 76C. End wall 76B is provided with a pair of horizontal grooves 78. The opposed end wall 76C has a similar pair of horizontal grooves 80. The significance of grooves 78 and 80 will be described hereinafter.

An upper edge 76D of the manifold housing 76 is coplanar with the upper edge 56B of the base plate 56. The manifold housing 76 has a lower edge 76E that is opposed to the upper edge 76D. A rectangular-shaped opening 82 extends inwardly from the upper edge 76D part way through the height of the manifold housing. The rectangular-shaped opening 82 meets a row of six cylindrically-shaped openings (not shown) that extend the remainder of the height of the manifold housing 76 to the lower edge 76E thereof.

FIGS. 5 to 8 show the manifold 84 that resides in the manifold housing 76. The manifold 84 is a plate-shaped member of an electrically insulative material, for example Nylon, having first and second or front and back sidewall surfaces 84A, 84B, both extending to opposed third and fourth end wall surfaces 84C, 84D, the front and back sidewall surfaces and the end wall surfaces extending to opposed proximal and distal faces 84E and 84F (the proximal face 84E is closer to the horizontal base plate foot 54 of the base plate assembly 48 than the distal face 84F). Six linearly aligned via holes 86A, 86B, 86C, 86D, 86E and 86F extend through the height of the manifold 84 to the opposed proximal and distal faces 84E and 84F.

Figure 7:
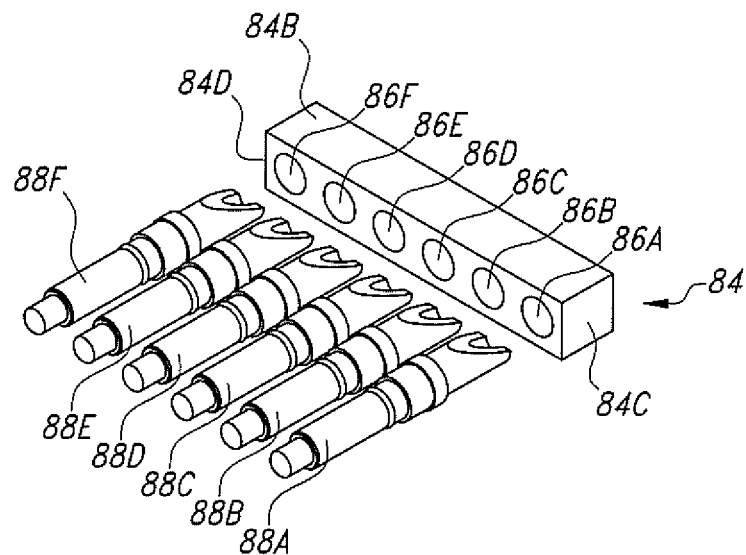
FIG. 7 is an exploded view of a manifold 84 for supporting electrical contact assemblies 88A, 88B, 88C, 88D, 88E and 88F.
Figure 8:
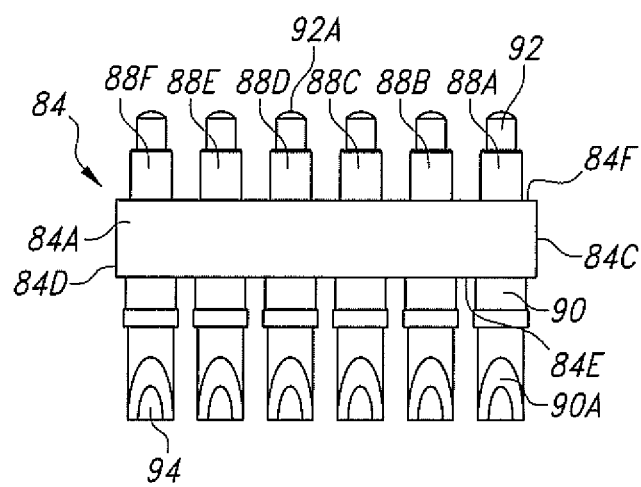
FIG. 8 is a front elevational view of the manifold 84 supporting the electrical contact assemblies 88A to 88F shown in FIG. 7.

FIGS. 7 and 8 show that the six via holes 86A, 86B, 86C, 86D, 86E and 86F in the manifold 84 are sized to receive a respective electrical contact assembly 88A, 88B, 88C, 88D, 88E and 88F. Each electrical contact assembly 88A to 88F is a rod-shaped or cylindrically-shaped structure comprising a contact sleeve 90 supporting a distal contact pin 92 in a spring-loaded relationship. The distal contact pin 92 has a partial hemispherical or dome-shaped end 92A. As will be described in detail hereinafter, the spring-loaded relationship of the distal contact pin 92 with the contact sleeve 90 enables the contact pin to actuate axially back and forth along the contact sleeve 90 without the two cylindrically-shaped members separating from each other.

Each contact sleeve 90 has a beveled proximal end 90A surrounding a bore hole 94 into which the bare end of a respective electrical conductor or wire 96A, 96B, 96C, 96D, 96E and 96F is received. The beveled end 90A provides an operator or robotic-controlled machine with a clear line-of-sight for making a secure electrical connection of the electrical conductor 96A to 96F to the electrical contact sleeve 90. Solder or a laser weld is preferred for making these electrical connections.

FIGS. 5 and 6 illustrate that the right-most or first electrical contact assembly 88A is connected to the first wire 96A which connects to a first electrical contact post 98. Contact post 98 extends through the right-side third vertical base plate wall 68A with its end seated in the right-side second vertical base plate wall 64A. An exposed terminal portion 98A of the first electrical contact post 98 resides in a first inlet formed between the right-side second and third vertical base plate walls 64A and 68A.

The next or second electrical contact assembly 88B is connected to the second wire 96B which connects to a second electrical contact post 100. Contact post 100 extends through the right-side second vertical base plate wall 64A with its end seated in the first horizontal base plate wall 60. An exposed terminal portion 100A of the second electrical contact post 100 resides in a second inlet formed between the right-side second vertical base plate wall 64A and the base plate wall 60.

The third electrical contact assembly 88C is connected to the third wire 96C which connects to a third electrical contact post 102. Contact post 102 extends through the base plate wall 60 with its end seated in the right extending portion of the base plate foot 54. An exposed terminal portion 102A of the third electrical contact post 102 resides in a third inlet formed between the base plate wall 60 and the base plate 54.

The fourth electrical contact assembly 88D is connected to the fourth wire 96D which connects to a fourth electrical contact post 104. Contact post 104 extends through the base plate wall 60 with its end seated in the left extending portion of the base plate foot 54. An exposed terminal portion 104A of the fourth electrical contact post 104 resides in a fourth inlet formed between the base plate foot 54 and the base plate wall 60.

The fifth electrical contact assembly 88E is connected to the fifth wire 96E which connects to a fifth electrical contact post 106. Contact post 106 extends through the left-side second vertical base plate wall 64B with its end seated in the first horizontal base plate wall 60. An exposed terminal portion 106A of the fifth electrical contact post 106 resides in a fifth inlet formed between the left-side second vertical base plate wall 64B and the base plate wall 60.

The left-most or sixth electrical contact assembly 88F is connected to the sixth wire 96F which connects to a sixth electrical contact post 108. Contact post 108 extends through the left-side third vertical base plate wall 68B with its end seated in the left-side second vertical base plate wall 64B. An exposed terminal portion 108A of the sixth electrical contact post 108 resides in a sixth inlet formed between the left-side second and third vertical base plate walls 64B, 68B.

Figure 9:
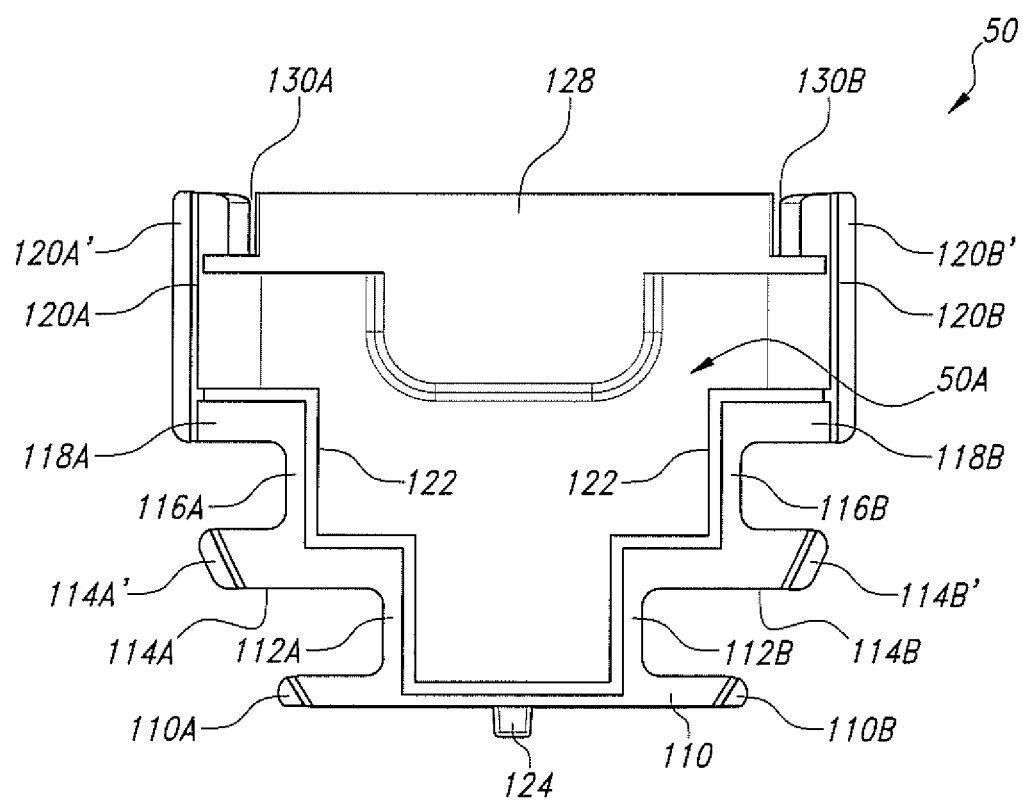
FIG. 9 is an elevational view of the inside of the cover plate 50 shown in FIGS. 3 and 4.

FIGS. 3, 4, 9 and 11 to 15 illustrate the cover plate 50. As particularly shown in FIG. 9 looking at its interior, the cover plate 50 comprises a proximal first horizontal cover plate wall 110 extending upwardly (out of the plane of the paper on which the drawing of FIG. 9 is rendered) from the peripheral edge of the cover plate. The first horizontal cover plate wall 110 has opposed extending fingers 110A and 110B. A first pair of opposed vertical cover plate webs 112A and 112B extending upwardly from the peripheral edge of the cover plate 50 connect from the proximal first horizontal cover plate wall 110 to a second pair of opposed horizontal cover plate walls 114A and 114B, which also extend upwardly from the peripheral edge of the cover plate 50. The second horizontal cover plate walls 114A, 114B have respective opposed extending fingers 114A', 114B'. The second pair of horizontal cover plate walls 114A, 114B connect to a second pair of opposed vertical cover plate webs 116A and 116B. The second pair of vertical cover plate webs 116A, 116B connect to a third pair of opposed horizontal cover plate walls 118A and 118B which, in turn, connect to a third pair of opposed vertical cover plate webs 120A and 120B. The third vertical cover plate webs 120A, 120B have respective opposed extending fingers 120A', 120B'. The third vertical cover plate webs 120A, 120B also extend upwardly from the peripheral edge of the cover plate 50 and terminate at a distal end of the cover plate.

As further shown in FIG. 9, a raised interior edge 122 delineates the proximal first horizontal cover plate wall 110, the first pair of vertical cover plate webs 112A, 112B, the second pair of horizontal cover plate walls 114A, 114B, the third pair of horizontal cover plate webs 116A, 116B, and the third pair of horizontal cover plate walls 118A, 118B from the inner surface 50A of the cover plate 50. A centered detent 124 extends proximally from the proximal first horizontal cover plate wall 110. To mate the cover plate 50 with the base plate 56, the detent 124 is received in a recess 126 in the base plate.

In the mated state shown in FIGS. 3 and 11 to 15 with the detent 124 of the cover plate 50 received in the recess 126 in the base plate 56, the landing area 74 of the first horizontal base plate wall 60 (FIG. 5) supports the proximal horizontal cover plate wall 110 of the cover plate 50. In the mated state, the first pair of vertical base plate webs 62A, 62B are aligned front-to-back with the first pair of vertical cover plate webs 112A, 112B, the second pair of horizontal base plate walls 64A, 64B are aligned front-to-back with the second pair of horizontal cover plate walls 114A, 114B, the second pair of vertical base plate webs 66A, 66B are aligned front-to-back with the second pair of vertical cover plate webs 116A, 116B, the third pair of horizontal base plate walls 68A, 68B are aligned front-to-back with the third pair of horizontal cover plate walls 118A, 118B, and the third pair of vertical base plate webs 70A, 70B are front-to-back aligned with the third pair of vertical cover plate webs 120A, 120B. The raised interior edge 122 of the cover plate 50 helps with this alignment as the cover plate is mated to the base plate assembly 48.

Further, with the cover plate 50 mated to the base plate 56, the extending fingers 110A and 110B of the first horizontal cover plate wall 110 are received in the opposed steps 60A and 60B of the first horizontal base plate wall 60, the extending fingers 114A', 114B' of the second horizontal cover plate walls 114A, 114B are received in the steps 64A' and 64B' of the second base plate walls 64A, 64B, and the extending fingers 120A', 120B' of the third vertical cover plate webs 120A, 120B are received in the steps 70A' and 70B' of the third vertical base plate webs 70A and 70B. As shown in the side elevational views of FIGS. 3 and 11 to 15, this mated structure provides the base plate assembly 48 connected to the cover plate 50 with an aesthetically contoured and continuously curved side that is easy to handle without any shape edges. The opposite side of the cover plate 50 mated to the base plate assembly 48 has a similarly aesthetic contour.

As further shown in FIG. 9, the cover plate 50 has a reliefed distal section 128 that is spaced above the inner surface 50A of the cover plate. The reliefed distal section 128 does not connect to the third pair of vertical cover plate webs 120A, 120B. Instead, there are opposed gaps 130A and 130B between the reliefed distal section 128 and the third pair of vertical cover plate webs 120A, 120B. Looking at the perspective view of the cover plate shown in FIG. 4, however, the reliefed distal section 128 is recessed below an outer surface 50B of the cover plate 50. The reliefed distal section 128 supports an oval-shaped visual indicator 132 which is molded from a different plastic than that which forms the body of the cover plate 50. The oval-shaped visual indicator 132 is centered in a reduced width portion of the reliefed distal section 128, proximate but distal the main outer surface 50B of the cover plate 50.

As shown in FIG. 6, the base plate 56 also has a reliefed distal section 134 that is spaced above the inner surface 56A of the base plate. The reliefed distal section 134 does not connect to the third pair of vertical base plate webs 70A, 70B. Instead, there are gaps 136A and 136B between the reliefed distal section 134 and the third pair of vertical base plate webs 70A, 70B. While not shown in the drawings, however, the reliefed distal section 134 is recess below an outer surface of the base plate 56.

In a similar manner as previously described for the cover plate 50, the reliefed distal section 134 supports an oval-shaped opaque visual indicator that is molded from a different plastic than that which forms the body of the base plate 56. This oval-shaped visual indicator is centered in a reduced width portion of the distal section 134, proximate but distal the main outer surface of the base plate 56. When the cover plate 50 is mated to the base plate assembly 48, the reliefed distal section 128 of the cover plate is aligned front-to-back with the reliefed distal section 134 of the base plate 56.

As shown in FIG. 6, with the six electrical contact assemblies 88A, 88B, 88C, 88D, 88E and 88F electrically connected to a respective one of the six electrical conductors or wires 96A, 96B, 96C, 96D, 96E and 96F, the dome-shaped distal end 92A of each of the distal contact pins 92 reside substantially along an imaginary line A-A. Further, the first exposed terminal portion 98A of the first electrical contact post 98 (indicated with raised indicia 1 on the cover plate 50 shown in FIGS. 3, 4, 11, 13 and 15) residing between the right-side second and third vertical base plate walls 64A and 68A, the second exposed terminal portion 100A of the second electrical contact post 100 (indicated with raised indicia 2) residing between the right-side second vertical base plate wall 64A and the base plate wall 60, the third exposed terminal portion 102A of the third electrical contact post 102 (indicated with raised indicia 3) residing between the base plate wall 60 and the base plate foot 54, the fourth exposed terminal portion 104A of the fourth electrical contact post 104 (indicated with raised indicia 4) residing between the base plate foot 54 and the base plate wall 60, the fifth exposed terminal portion 106A of the fifth electrical contact post 106 (indicated with raised indicia 5) residing between the left-side second vertical base plate wall 64B and the base plate wall 60, and the sixth exposed terminal portion 108A of the sixth electrical contact post 108 (indicated with raised indicia 6) residing between the left-side second and third vertical base plate walls 64B, 68B are visible to the physician or a company representative. similar raised indicia 1 to 6 reside on the base plate assembly 48.

Figure 10:
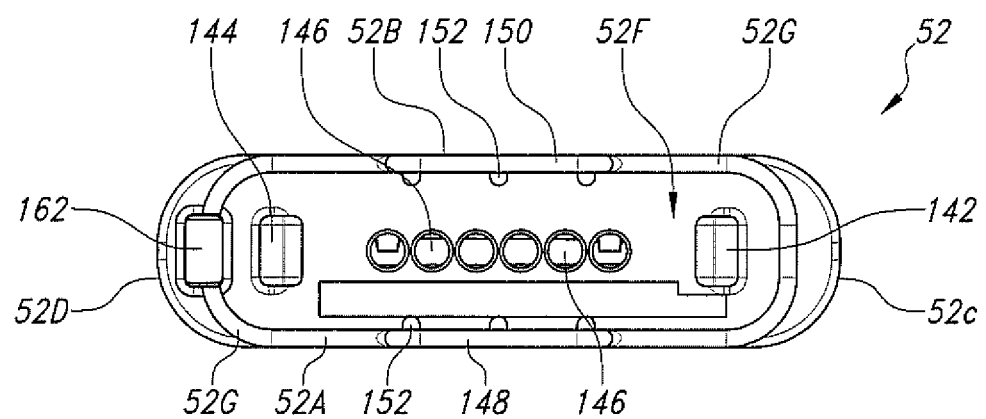
FIG. 10 is a plan view of the inside of the header 52 shown in FIG. 9.
Figure 12:
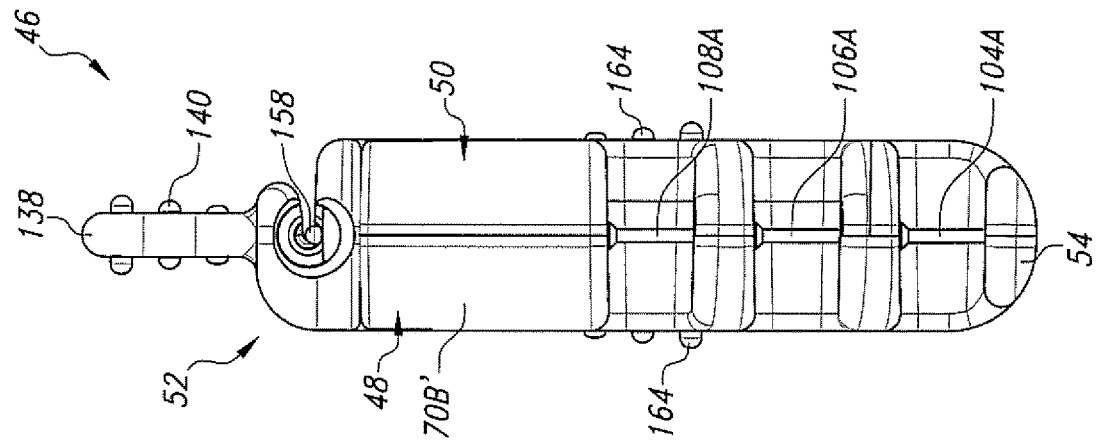
FIG. 12 is a side elevational view of the closed lead adapter 46 shown in FIG. 11.
Figure 11:
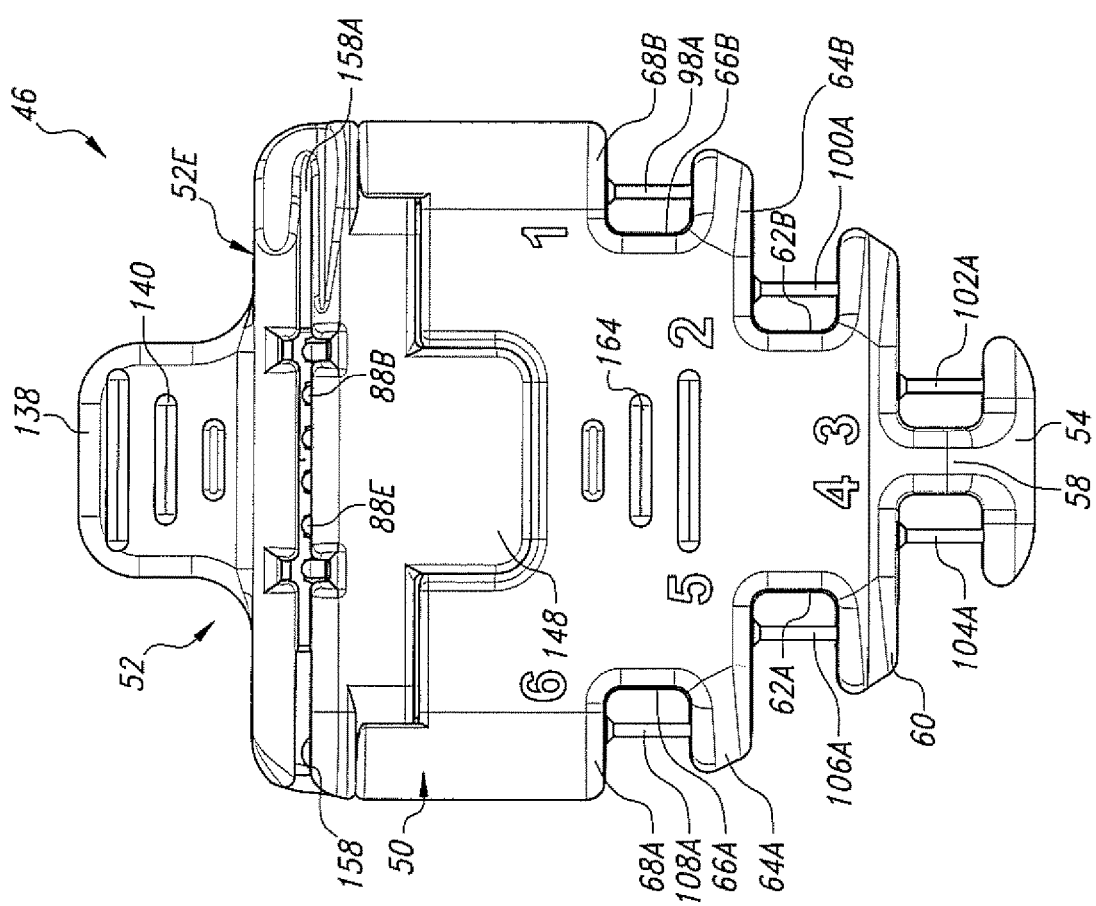
FIG. 11 is a front elevational view of the lead adapter 46 shown in FIG. 3 in a closed position.
Figure 15:
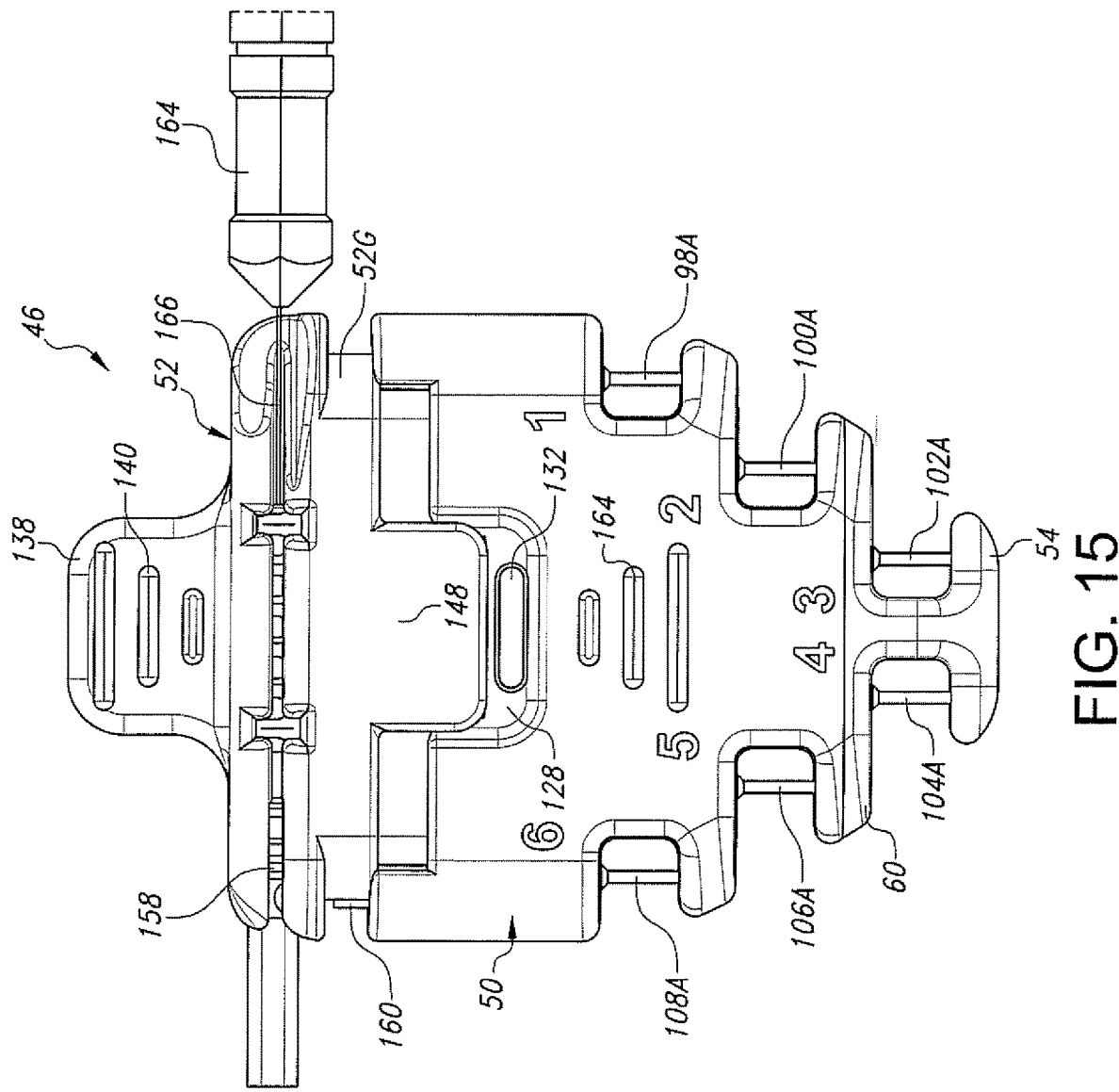
FIG. 15 is a front elevational view of the open lead adapter 46 shown in FIGS. 13 and 14 receiving an implantable lead 18.

As shown in FIGS. 3, 4 and 10 to 15, the open-ended housing formed from the base plate assembly 48 connected to the cover plate 50 of the lead adapter 46 is closed with the header 52. As particularly shown in FIG. 4, the header 52 is a generally oval-shaped plate comprising opposed long and generally straight sidewalls 52A, 52B meeting opposed curved end walls 52C, 52D. The sidewalls 52A, 52B and the end walls 52C, 52D meet an upper surface 52E spaced from an inner surface 52F (FIG. 10). A skirt 52G depends from the sidewall 52A, 52B and the curved end wall 52C. A finger tab 138 extends upwardly from the upper surface 52F of the header 52. The finger tab 138 has a number (for example three) of aligned outwardly facing horizontal ridges 140 on each of its opposed major sides that aid in tactile feel and gripping manipulation of the header 52.

As shown in FIG. 10, inwardly facing L-shaped hooks 142, 144 depend from the inner surface 52F of the oval-shaped plate proximate the curved end walls 52C, 52D. The inner surface 52F of the header is provided with a plurality of recesses or inlets 146 (FIG. 10) into which the distal ends of the electrical contact assemblies 88A to 88F nest with the header 52 in the closed position shown in FIGS. 3, 11 and 12, but without the header having received an implantable lead 18 as will be described in detail hereinafter.

There is also a pair of tabs 148, 150 (FIGS. 3, 4, 10, 11, 13 and 15) that depend from the skirt 52G of the header 52 centered about midway along the length of the straight sidewalls 52A, 52B. The tabs 148, 150 are sized to be received in the respective reliefed distal section 128 of the cover plate and the aligned reliefed distal section 134 of the base plate 56.

Figure 4:
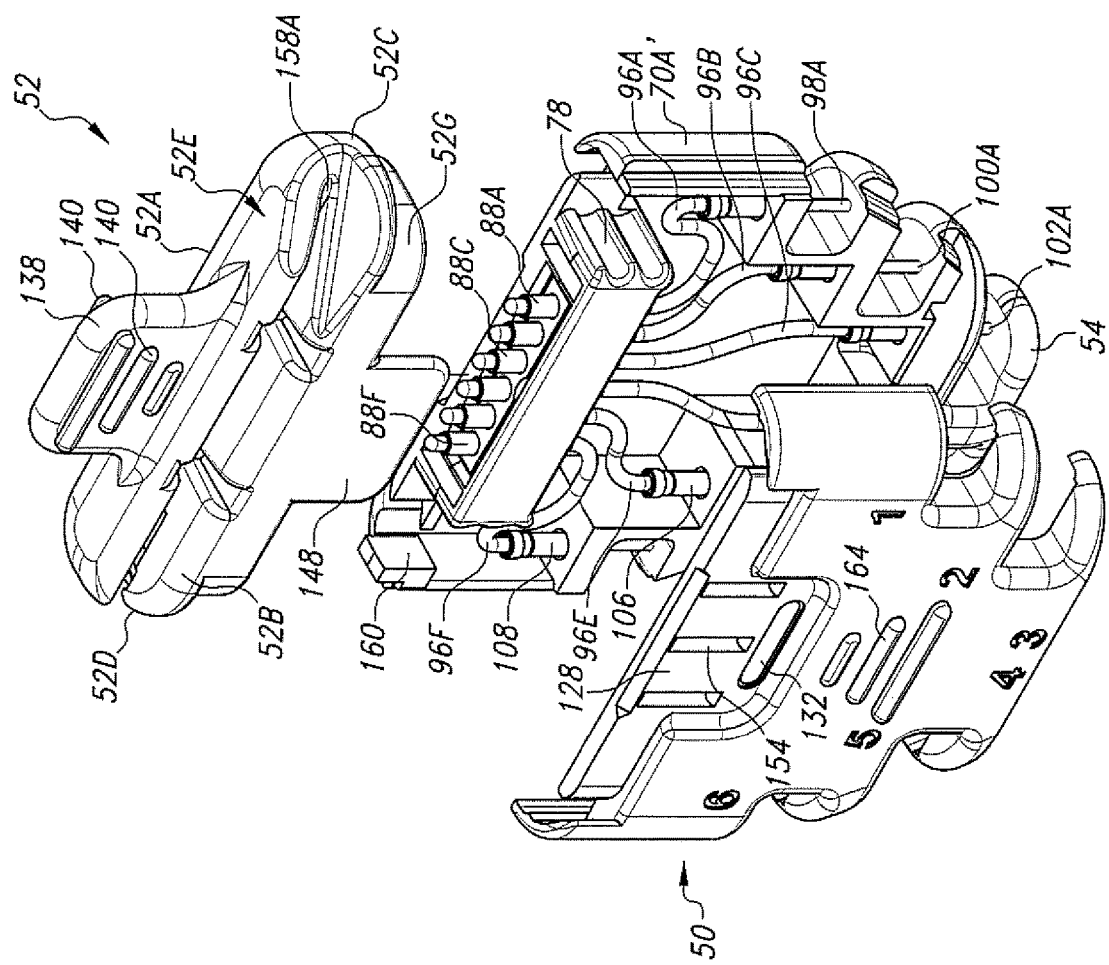
FIG. 4 is an exploded view of the lead adapter 46 shown in FIG. 3.
Figure 3:
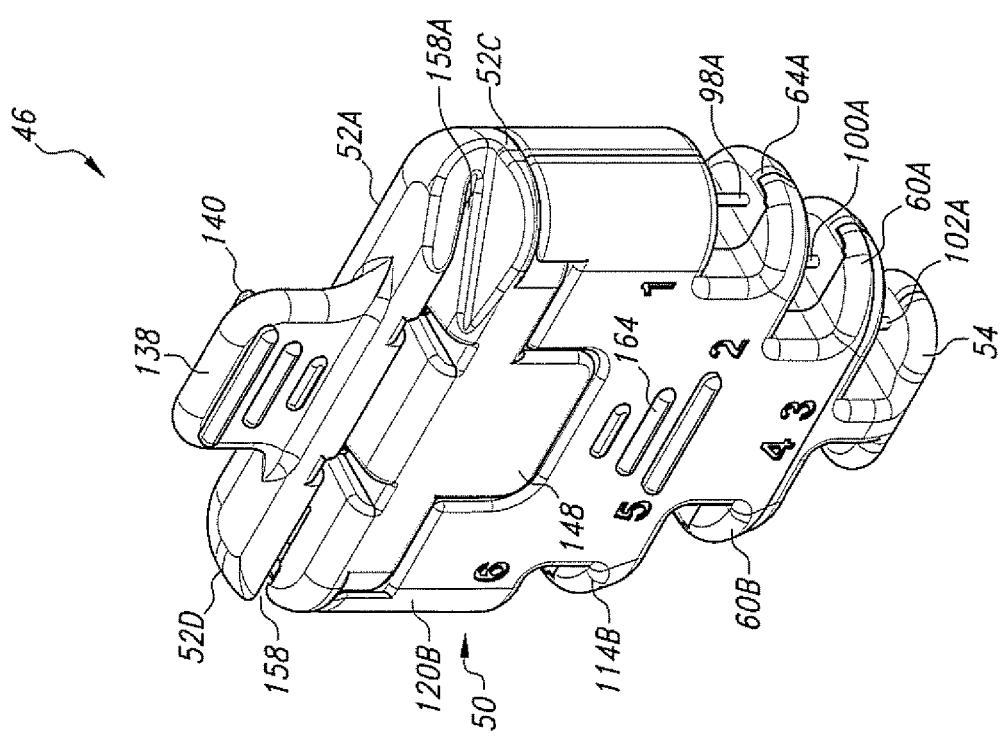
FIG. 3 is a front elevational view of a lead adapter 46 comprising a base plate assembly 48 connected to a cover plate 50 to thereby form an open-ended housing closed by a header 52 according to the present invention.

The tabs 148, 150 are each provided with a number (for example three) of inwardly facing aligned vertical ridges 152 that mate with corresponding outwardly facing aligned vertical grooves 154 in the base plate 56 and the cover plate 50 (only shown in the cover plate 50 in FIG. 4). With the vertical ridges 152 having been moved proximally along the length of the vertical grooves 154, the L-shaped hooks 142, 144 snap-fit into engagement with one of the two opposed horizontal grooves 78, 80 on the manifold housing 76. That is, the inwardly facing L-shaped hooks 142, 144 are manipulatable to selectively engage the opposed horizontal grooves 78, 80 of the manifold housing 76 in a snap-fit engagement. The closed position for the lead adapter 46 is when the L-shaped hooks 142, 144 are in a snap-fit engagement with a proximal most one (closest to the horizontal base plate foot 54 and the proximal first horizontal cover plate wall 110) of the opposed horizontal grooves 78, 80 while the open position for the lead adapter 46 occurs when the L-shaped hooks 142, 144 are in a snap-fit engagement with a distal most one of the horizontal grooves 78, 80.

As the L-shaped hooks 142, 144 are move proximally with respect to the horizontal grooves 78, 80 to put the lead adapter 46 in the closed position, the skirt 52G of the header 52 is also received in the opposed gaps 130A and 130B between the reliefed distal section 128 and the third pair of vertical cover plate webs 120A, 120B and in the opposed gaps 136A and 136B between the reliefed distal section 134 and the third pair of vertical base plate webs 70A, 70B of the base plate assembly 48. In contrast, as the L-shaped hooks 142, 144 are move distally with respect to the horizontal grooves 78, 80 to put the lead adapter 46 in the opened position, the skirt 52G of the header 52 is removed from the opposed gaps 130A and 130B between the reliefed distal section 128 and the third pair of vertical cover plate webs 120A, 120B and from the opposed gaps 136A and 136B between the reliefed distal section 134 and the third pair of vertical base plate webs 70A, 70B of the base plate assembly 48.

As shown in FIGS. 3, 4 and 11 to 15, the header 52 is further provided with a longitudinally-extending opening 158 that extends inwardly into the curved end wall 52D to a tapered end 158A adjacent to the curved end wall 520 of the header. A registration tab 160 (FIGS. 4 to 6, 13 and 15) extends upwardly from the third vertical base plate web 70B of the base plate 56 and is received in a matching recess 162 (FIG. 10) in the header 52. Recess 162 resides adjacent to the longitudinally-extending opening 158 and serves as a stop to prevent the proximal end of the implantable lead 18 from being moved into the opening 158 with the header 52 in a closed position seated on the open-ended housing formed from the base plate assembly 48 connected to the cover plate 50.

In Use

The lead adaptor 46 of the present invention is first connected to an exemplary external trial stimulator 34 as shown in FIG. 2 using a number of off-the-shelf temporary extension cables 36. The temporary extension cable 36 has a proximal male shrouded pin 37 that is connected to the external trial stimulator 34 while the distal alligator clip 38 is connected to one of the first, second, third, fourth, fifth and sixth exposed terminal portions 98A, 100A, 102A, 104A, 106A and 108A of the respective first, second, third, fourth, fifth and sixth electrical contact posts 98, 100, 102, 104, 106 and 108 (indicated with respective raised indicia 1, 2, 3, 4, 5 and 6). An exemplary temporary extension cable 36 is marketed by Oscor Inc., Palm Harbor, Florida, as the ATAR™ D-R D2P connection cable. Unlike the previously discussed cable assembly of the '290 patent where the proximal connector must be compatible with a particular external trial stimulator, which means that an operating room must keep a number of the prior art cable assemblies readily available for connection to any one of a number of external trial stimulators, the temporary extension cable 36 shown in FIG. 2 is configured to connect to any one of a number of different external trial stimulators. This greatly reduces the number of temporary extension cables that must be kept on hand in an operating room.

The practitioner then holds the housing of the lead adapter 46 with one hand and with the other hand grasps the finger tab 138 to move the header 52 into the open position. This fully open position is apparent to the practitioner when the opposed visual indicators 132 centered in the reduced width portion of the reliefed distal section 128 of the cover plate 50 and in the reduced width portion of the distal section 134 of the base plate 56 (FIGS. 4, 13 and 15) are visible.

With the lead adaptor 46 now in the open position, the practitioner holds the lead adaptor in one hand and with the other hand holding the handle 164 of a stylet 166 (FIG. 15), inserts the stylet into the tapered end 158A of the longitudinally-extending opening 158. With the stylet 166 residing in the longitudinally-extending opening 158, the practitioner inserts the proximal electrical contacts of an implantable lead 18 into the opening 158 with a lumen of the lead receiving the stylet. The proximal electrical contacts of the lead 18 are moved into the opening 158 until the lead "bottoms out" at the tapered end 158A of the opening adjacent to the curved end wall 52C of the header 52.

The practitioner then pushes on the finger tab 138 to move the header into the closed position, seated on the distal open end of the housing formed from the base plate assembly 48 connected to the cover plate 50. This movement brings the electrodes 20 of the implantable lead 18 into firm electrical contact with the spring-loaded electrical contact assemblies 88A to 88F housed inside the lead adaptor 46. As previously described, the spring-loaded relationship of the distal contact pins 92 with the contact sleeves 90 of the six electrical contact assemblies 88A to 88F enables each contact pin 92 to actuate axially back and forth along its contact sleeve 90 as the header 52 supporting the implantable lead 18 is moved from the open to the closed position and back to the open position. This enables the electrodes 20 at the proximal end of the implantable lead 18 to ride over the dome-shaped ends 92A of the distal contact pins 92 to help ensure that the contact pins are in electrical continuity with the implantable lead 18. The practitioner is now ready to test the efficacy of the implantable lead 18 in an initial position at a body tissue site.

Thus, with the header 52 in the open position, the dome-shaped distal ends 92A of the electrical contact assemblies 88A to 88F reside along the first imaginary line A-A shown in FIG. 6 spaced distally outwardly with respect to the upper edge 76D of the manifold housing 76 of the base plate assembly 48. Conversely, with the header 52 in the closed position, the distal ends 92A of the electrical contact assemblies 88A to 88F reside along a second imaginary line (not shown) that is spaced closer to the upper edge 76D of the manifold housing 76 than when the header 52 is in the open position with the plurality of electrical contact assemblies 88A to 88F residing along the first imaginary line A-A.

If needed, the practitioner can disconnect the lead adapter 46 from the implantable lead 18, reposition the lead in the body tissue, reconnect the lead adapter 46 and reapply electrical stimulation from the external trial stimulator 34 to the body tissue. This process is performed iteratively until the practitioner obtains the desired position for the implantable lead 18.

As previously described, in a representative protocol the patient 12 receives therapy for a limited trial period, for example a one-week trial period, during which time the patient wears the lead adapter 46 and the external trial stimulator 34 outside the body. Assuming the trial therapy is effective or shows the promise of being effective, the practitioner then replaces the external trial stimulator 34 and the lead adapter 46 with the implanted pulse generator 16 connected to the implantable lead 18 or connected to the lead extension 22 in turn connected to the implantable lead, and programs the pulse generator 16 with parameters selected based on the experience gained during the trial period. Optionally, the practitioner can also replace the implantable lead 18.

It is appreciated that various modifications to the inventive concepts described herein may be apparent to those of ordinary skill in the art without departing from the scope of the present invention as defined by the appended claims.

What is claimed is:

1. A lead adapter for a patient treatment system, the lead adapter comprising:
    a) a housing extending from a housing proximal end to a housing distal portion having a housing distal open end, wherein the housing has a plurality of inlets, each inlet being segregated from an immediately adjacent inlet by a housing intermediate wall;
    b) a plurality of electrical contact assemblies residing in the housing, the plurality of electrical contact assemblies being electrically connected to a respective one of a plurality of electrical contact posts, wherein the plurality of electrical contact posts each have an exposed terminal portion residing in a respective one of the plurality of inlets; and
    c) a header that is movably secured to the housing distal portion to selectively open and close the housing distal open end as the header is manipulated from a closed position to an open position and is further manipulated from the open position to the closed position, wherein the header has at least one longitudinally extending opening that is configured to receive a proximal end of an implantable lead,
    d) wherein with the header in the open position, the proximal end of the implantable lead is movable into the longitudinally extending opening, and wherein the header is then manipulatable into the closed position to move an electrical contact of the implantable lead into contact with a respective one of the plurality of electrical contact assemblies electrically connected to a respective one of the plurality of electrical contact posts so that the electrical contact of the implantable lead is in electrical continuity with an exposed terminal portion of a respective one of the plurality of electrical contact posts.

2. The lead adapter of claim 1, wherein, with the header in the open position, distal ends of the plurality of electrical contact assemblies reside along a first imaginary line spaced distally outwardly with respect to the housing distal open end, and wherein with the header in the closed position, the distal ends of the plurality of electrical contact assemblies reside along a second imaginary line that is spaced closer to the housing distal open end than when the header is in the open position with the plurality of electrical contact assemblies residing along the first imaginary line.

3. The lead adapter of claim 1, wherein a manifold is disposed inside the housing, the manifold comprising a plurality of via holes that receive one of the electrical contact assemblies.

4. The lead adapter of claim 3, wherein the manifold has two opposed horizontal grooves on an outer surface thereof, and wherein the header has a pair of inwardly facing L-shaped hooks that are in selective snap-fit engagement with the two opposed horizontal grooves to thereby define the closed position for the lead adapter with the L-shaped hooks in a snap-fit engagement with a proximal most one of the two horizontal grooves and to define the open position for the lead adapter with the L-shaped hooks of the header in a snap-fit engagement with a distal most one of the two horizontal grooves.

5. The lead adapter of claim 1, wherein the housing is provided with two visual indicators, one of them on opposed sides of the housing.

6. The lead adapter of claim 5, wherein a pair of opposed tabs depending from the header are configured to cover the visual indicators with the header in the closed position and to expose the visual indicators with the header in the open position.

7. The lead adapter of claim 6, wherein the opposed tabs depending from the header each support at least one inwardly facing vertical ridge that mates with an outwardly facing vertical groove in the housing.

8. The lead adapter of claim 1, wherein a finger tab extending outwardly from the header aids in manipulation of the header between the open and closed positions.

9. The lead adapter of claim 1, wherein the housing is comprised of a base plate mated to a cover plate to thereby define the housing distal open end.

10. The lead adapter of claim 1, wherein, with the header in the closed position, a registration tab extending upwardly from the housing adjacent to the housing distal open end is received in a matching recess in the header, and wherein, with the header in the open position, the registration tab resides outside the matching recess.

11. A lead adapter for a patient treatment system, the lead adapter comprising:
   a) a housing extending from a housing proximal end to a housing distal portion having a housing distal open end, wherein the housing comprises at least a first inlet segregated from a second inlet by a housing intermediate first wall;
   b) at least a first electrical contact assembly and a second electrical contact assembly residing in the housing, the first and second electrical contact assemblies being electrically connected to respective first and second electrical contact posts, wherein the first electrical contact post has an exposed first terminal portion residing in the first inlet and the second electrical contact post has an exposed second terminal portion residing in the second inlet; and
   c) a header that is movably secured to the housing distal portion to selectively open and close the housing distal open end as the header is manipulated from a closed position to an open position and is further manipulated from the open position to the closed position, wherein the header has at least one longitudinally extending opening that is configured to receive a proximal end of an implantable lead,
   d) wherein with the proximal end of the implantable lead received in the longitudinally extending opening in the header, a first electrical contact of the implantable lead is in electrical continuity with the exposed first terminal portion of the first electrical contact post and a second electrical contact of the implantable lead is in electrical continuity with the exposed second terminal portion of the second electrical contact post.

12. The lead adapter of claim 11, wherein the housing further comprises at least a third inlet segregated from a fourth inlet by a housing intermediate second wall, and wherein a third electrical contact assembly and a fourth electrical contact assembly reside in the housing, the third and fourth electrical contact assemblies being electrically connected to a respective third and fourth electrical contact posts, wherein the third electrical contact post has an exposed third terminal portion residing in the third inlet and the fourth electrical contact post has an exposed fourth terminal portion residing in the fourth inlet,
   wherein with the proximal end of an implantable lead received in the longitudinally extending opening in the header, a third electrical contact of the implantable lead is in electrical continuity with the exposed third terminal portion of the third electrical contact post and a fourth electrical contact of the implantable lead is in electrical continuity with the exposed fourth terminal portion of the fourth electrical contact post.

13. The lead adapter of claim 12, wherein the first and second electrical contact posts reside in a first side of the housing, and the third and fourth contact posts reside in an opposite second side of the housing.

14. The lead adapter of claim 12, wherein, with the header in the open position, distal ends of the first, second, third and fourth electrical contact assemblies reside along a first imaginary line spaced distally outwardly with respect to the housing distal open end, and wherein with the header in the closed position, the distal ends of the first, second, third and fourth electrical contact assemblies reside along a second imaginary line that is spaced closer to the housing distal open end than when the header is in the open position with the first, second, third and fourth electrical contact assemblies residing along the first imaginary line.

15. The lead adapter of claim 11, wherein a manifold is disposed inside the housing, the manifold comprising at least two via holes that receive one of the first and second electrical contact assemblies.

16. The lead adapter of claim 15, wherein the manifold has two opposed horizontal grooves on an outer surface thereof, and wherein the header has a pair of inwardly facing L-shaped hooks that are in selective snap-fit engagement with the two opposed horizontal grooves to thereby define the closed position for the lead adapter with the L-shaped hooks in a snap-fit engagement with a proximal most one of the two horizontal grooves and to define the open position for the lead adapter with the L-shaped hooks of the header in a snap-fit engagement with a distal most one of the two horizontal grooves.

17. The lead adapter of claim 11, wherein the housing is provided with two visual indicators, one of them on opposed sides of the housing.

18. The lead adapter of claim 17, wherein a pair of opposed tabs depending from the header are configured to cover the visual indicators with the header in the closed position and to expose the visual indicators with the header in the open position.

19. The lead adapter of claim 11, wherein the opposed tabs depending from the header each support at least one inwardly facing vertical ridge that mates with an outwardly facing vertical groove in the housing.

20. A lead adapter for a patient treatment system, the lead adapter comprising:
   a) a housing extending from a housing proximal end to a housing distal portion having a housing distal open end, wherein the housing comprises:
      i) at least a first inlet segregated from a second inlet by a housing intermediate first wall, wherein a first electrical contact assembly and a second electrical contact assembly reside in the housing, the first and second electrical contact assemblies being electrically connected to respective first and second electrical contact posts, and wherein the first electrical contact post has an exposed first terminal portion residing in the first inlet and the second electrical contact post has an exposed second terminal portion residing in the second inlet; and
      ii) at least a third inlet segregated from a fourth inlet by a housing intermediate second wall, wherein a third electrical contact assembly and a fourth electrical contact assembly reside in the housing, the third and fourth electrical contact assemblies being electrically connected to respective third and fourth electrical contact posts, and wherein the third electrical contact post has an exposed third terminal portion residing in the third inlet and the fourth electrical contact post has an exposed fourth terminal portion residing in the fourth inlet,
      iii) wherein the first and second electrical contact posts reside in a first side of the housing, and the third and fourth contact posts reside in an opposite second side of the housing;
   b) at least a first, a second, a third and a fourth electrical contact assembly residing in the housing, the first, second, third and fourth electrical contact assemblies being electrically connected to a respective first, second, third and fourth electrical contact posts, wherein the first electrical contact post has an exposed first terminal portion residing in the first inlet, the second electrical contact post has an exposed second terminal portion residing in the second inlet, the third electrical contact post has an exposed third terminal portion residing in the third inlet, and the fourth electrical contact post has an exposed fourth terminal portion residing in the fourth inlet, wherein the first and second electrical contact posts reside in a first side of the housing, and the third and fourth contact posts reside in an opposite second side of the housing; and c) a header that is movably secured to the housing distal portion to selectively open and close the housing distal open end as the header is manipulated from a closed position to an open position and is further manipulated from the open position to the closed position, wherein the header has at least one longitudinally extending opening that is configured to receive a proximal end of an implantable lead, d) wherein with the proximal end of the implantable lead received in the longitudinally extending opening in the header, a first, a second, a third and a fourth electrical contacts of the implantable lead are in electrical continuity with the respective exposed first, second, third and fourth terminal portions of the first, second, third and fourth electrical contact posts.

21. The lead adapter of claim 20, wherein, with the header in the open position, distal ends of the first, second, third and fourth electrical contact assemblies reside along a first imaginary line spaced distally outwardly with respect to the housing distal open end, and wherein with the header in the closed position, the distal ends of the first, second, third and fourth electrical contact assemblies reside along a second imaginary line that is spaced closer to the housing distal open end than when the header is in the open position with the first, second, third and fourth electrical contact assemblies residing along the first imaginary line.

* * * * *